United States Patent [19]

Deckers et al.

[11] Patent Number: 5,498,587
[45] Date of Patent: Mar. 12, 1996

[54] HYDROGENATION CATALYST, A PROCESS FOR ITS PREPARATION, AND USE THEREOF

[75] Inventors: Gregor Deckers, Xanten; Gerhard Diekhaus, Oberhausen; Bernd Dorsch, Bottrop; Carl D. Frohning, Wesel; Gerhardt Horn; Horst B. Horrig, both of Oberhausen, all of Germany

[73] Assignee: Hoechst Aktiengesellschaft, Germany

[21] Appl. No.: 217,151

[22] Filed: Mar. 24, 1994

[30] Foreign Application Priority Data

Mar. 27, 1993 [DE] Germany .................. 43 10 053.8

[51] Int. Cl.$^6$ .................. B01J 21/10; B01J 23/04; B01J 23/78
[52] U.S. Cl. .................. 502/328; 502/330; 502/337; 502/340; 502/344; 568/885
[58] Field of Search .................. 502/328, 330, 502/335, 337; 568/885

[56] References Cited

U.S. PATENT DOCUMENTS

| 3,868,332 | 2/1975 | Carter et al. ............... 252/452 |
| 3,926,583 | 12/1975 | Rostrup-Nielsen ............ 502/328 |
| 4,216,123 | 8/1980 | Banks et al. ............... 502/330 |
| 4,703,031 | 10/1987 | Unmuth et al. ............. 502/339 |
| 5,004,719 | 4/1991 | Deller et al. .............. 502/349 |
| 5,244,648 | 9/1993 | Dupin et al. .............. 502/355 |

FOREIGN PATENT DOCUMENTS

| 114704 | 8/1984 | European Pat. Off. . |
| 340848 | 11/1989 | European Pat. Off. . |
| 389158 | 9/1990 | European Pat. Off. . |
| 398668 | 11/1990 | European Pat. Off. . |
| 470344 | 2/1992 | European Pat. Off. . |
| 472918 | 3/1992 | European Pat. Off. . |

*Primary Examiner*—Anthony McFarlane
*Attorney, Agent, or Firm*—Bierman and Muserlian

[57] ABSTRACT

A hydrogenation catalyst comprising 25 to 50% by weight of nickel (metallic) 10 to 35% by weight of nickel oxide 4 to 12% by weight of magnesium oxide 1 to 5% by weight of sodium oxide the remainder being a water-insoluble support material, wherein the total of nickel and nickel oxide is 40% to 70% by weight, and the catalyst has a surface area, determined by BET, of 80 to 200 m$^2$/g and a total pore volume of 0.35 to 0.6 ml/g. The total pore volume is made up of 30% to 60% by volume from pores having pore radii of $\leq$40 Å, 4% to 10% by volume from pores having pore radii of >40 to 300 Å, and 30% to 60% by volume from pores having pore radii of >300 to 5000 Å.

A process for preparing the hydrogenation catalyst which comprises preparing, in a precipitation step, a green catalyst from a nickel salt, a magnesium salt, sodium carbonate, and the support material, separating off the mother liquor and partially washing the precipitate, slurrying the green catalyst in alkali solution, separating it from the liquid phase, drying it, and contacting the dried green catalyst with hydrogen until 48% to 86% by weight of the total nickel content is present in metallic form.

The hydrogenation catalyst of the invention is particularly suitable for the hydrogenation of propanal, n-butanal, and i-butanal, especially at temperatures between 100° and 160° C.

11 Claims, No Drawings

HYDROGENATION CATALYST, A PROCESS FOR ITS PREPARATION, AND USE THEREOF

This Application claims the benefit of the priority of German Application P 43 10 053.8, filed Mar. 27, 1993.

The present invention relates to a reduced hydrogenation catalyst comprising nickel, nickel oxide, magnesium oxide, and a water-insoluble support material, a method of its preparation and the preferred use thereof in the hydrogenation of certain aldehydes.

BACKGROUND OF THE INVENTION

Catalysts based on nickel as the active catalyst component for the hydrogenation of aldehydes are part of the prior art. For example, EP-A-322 049 describes a hydrogenation catalyst comprising 1) a molar ratio of $SiO_2/Ni=0.15-0.35$
2) a molar ratio of $(Mg\ or\ Ba)/Ni=0-0.15$, in which part of the nickel is present in metallic form.

The known hydrogenation catalysts based on nickel can be used in the hydrogenation of aldehydes only at temperatures up to about 100° C., since increasing the hydrogenation temperature leads to the formation of undesired by-products which can sometimes only be removed by complicated distillation.

SUMMARY OF THE INVENTION

It was, therefore, an object of the invention to provide a hydrogenation catalyst which has high selectivity and produces conversions of over 99.5% with high throughput rates at hydrogenation temperatures above 110° C.

This object is surprisingly achieved by means of a hydrogenation catalyst containing 25% to 50% by weight of (metallic) nickel
10% to 35% by weight of nickel oxide
4% to 12% by weight of magnesium oxide
1% to 5% by weight of sodium oxide
The reminder is support material.

The total of nickel and nickel oxide is from 40% to 70% by weight, the surface area (determined by BET) is 80 to 200 $m^2/g$, and the total pore volume (determined by Hg porosimetry) is 0.35 to 0.6 ml/g. The total pore volume is made up of 30% to 60% by volume of pores having pore radii $\leq 40$ Å, 4% to 10% by volume of pores having pore radii of more than 40 and up to 300 Å, and 30% to 60% by volume of pores having pore radii of more than 300 and up to 5000 Å.

The hydrogenation catalyst of the invention preferably has the following further characteristics:

a) 5 to 10 atomic layers on the surface of the hydrogenation catalyst contain, as determined by SAM analysis, 18 to 30, preferably 20 to 28, atom % Ni, 1.2 to 3.0, preferably 1.5 to 2.5, atom % Na, and 2.8 to 4.8, preferably 3.2 to 4.5, atom % Mg;

b) the metallic nickel surface area is, as determined by chemisorption of hydrogen, 100 to 130 $m^2/g$ Ni;

c) the catalyst contains aluminium oxide or silicon dioxide, particularly in the form of silicic acid, silica gel, kieselguhr, or siliceous earth, as the support material.

The invention further relates to a process for producing the hydrogenation catalyst, which comprises preparing, in a precipitation step, a green catalyst from a nickel salt, a magnesium salt, sodium carbonate, and the support material, separating off the mother liquor and partially washing the precipitate, slurrying the green catalyst in alkali solution, separating it from the liquid phase, drying it, and contacting the dried green catalyst with hydrogen until 42% to 83% by weight of the total nickel content is present in metallic form.

In a preferred form of the process, an aqueous solution, at 95° to 100° C. containing 0.5 to 0.8 mols/liter of a nickel salt and 0.1 to 0.2 mols/liter of a magnesium salt, is stirred into a 0.9 to 1.1 molar sodium carbonate solution, also at 95° to 100° C., until the molar ratio of $Na_2CO_3/(Ni+Mg)$ is 1:0.60 to 0.65. The support material is immediately added over a period of 0.5 to 5 minutes and the green catalyst formed is filtered off from the mother liquor and partially washed with hot water until the effluent wash water has a conductivity from 1500 to 2000 µS. The green catalyst is then suspended in 1 to 3 times its volume of water and either 0.06 to 0.08 mol of sodium hydroxide solution or 0.03 to 0.04 mol of sodium carbonate per mol of nickel used in the precipitation step is stirred in. After stirring for 1 to 5 hours at 40° to 60° C., the green catalyst is separated off from the suspension.

After drying, the green catalyst which has been separated off from the suspension is reduced at 350° to 450° by treatment with 0.5 to 5.0 standard $m^3$/hour of reduction gas per kilogram of green catalyst; the reduction gas contains 80% to 100% by volume of hydrogen. Most preferably, 1 to 3 standard $m^3$/hour of reduction gas is used per kilogram of the dried green catalyst. For better shaping, 0.5% to 5% by weight of graphite may be added to the hydrogenation catalyst.

The hydrogenation catalyst of the invention is particularly useful for the hydrogenation of propanal, n-butanal, and i-butanal, preferably at 110° to 160° C. This reaction can be carried out with simultaneous generation of steam under pressure to improve the economics of the process. In comparison with conventional hydrogenation catalysts, the hydrogenation can be carried out at increased catalyst loads of 0.8 to 1.0 kilograms/hour of aldehyde per kilogram of catalyst. The selectivity is greater than 99.5%, usually greater than 99.9%; about 0.01% of the aldehyde used remains in the final product. Less than 0.1% of the aldehyde is converted into carbon monoxide, ethers, acetals, and esters. Moreover, in the hydrogenation of n-butanal, the formation of dibutyl ether is less than 50 ppm, allowing distillation of the final product to be omitted. In the hydrogenation of n-propanal, the formation of dipropyl ether is less than 20 ppm.

The analytical methods employed are as follows:
1. BET determination of surface area The method for determining the BET total surface area according to Brunauer, Emmett and Teller is described in *J. Amer. Chem. Soc.* 60 (1938), page 309.

2. Determination of pore volume by Hg porosimetry (total pore volume and pore distribution)

The method for the determination of pore volume by Hg porosimetry up to 3900 bar is according to H. L. Ritter, L. C. Drake and is described in *Ind. Engng. chem. analyt.* Edit, 17 (1945) 782.

3. Determination of surface area by chemisorption

The method for determining the surface area of the nickel by chemisorption, viz. the amount of hydrogen adsorbed at 20° C., is described in J. of Catalysis 81 (1983) 204 and 96 (1985) 517.

4. Determination of pore radius

The method for the determination of pore radius is described by S. J. Gregg, K. S. W. Sing, Adsorption Surface Area and Porosity, Academic Press New York-London (1967), pages 160 to 182.

5. Surface analysis by SAM spectroscopy (Scanning Auger Microprobe)

The analyses were carried out with a SAM spectrometer model PHI 660 from Perkin-Elmer.

The chamber, into which the samples are placed, is evacuated to $\leq 1\times 10^{-8}$ torr by a turbomolecular pump. An electron gun produces an electron beam which is fired at the sample. Because of strong charging of the samples by the stream of electrons, MULTIPLEX measurements are carried out at 5 different points on each sample; however, only the energy ranges of the elements to be expected are scanned, so as to minimize the measurement time as much as possible.

The measurement and analysis of the AUGER electrons emitted from the sample is carried out by means of a cylindrical mirror analyzer. The following conditions were selected in the analyses:

Energy resolution (E/E): 0.6%

Activation energy: 10 kV/10 mA

Lateral resolution: about 220 nm

The quantitative evaluation was based on the sensitivity factors of the pure elements, which are published in the "Handbook of Auger Spectroscopy". The corresponding values for the elements nickel, sodium and magnesium were measured and evaluated. The SAM analysis method is described in detail in "Practical Surface Analysis by Auger and X-ray photoelectronic Spectroscopy" by D. Briggs and M. Seah, John Wiley and Sons, New York, London (1983), pages 217 ff. and 283 ff.

Properties of the hydrogenation catalyst

The specific physical and chemical properties of the hydrogenation catalyst, which in the final analysis are the prerequisites for its advantageous hydrogenation behavior, are desirably achieved by the following features and measures in its preparation.

In the precipitation step, the mixed basic nickel-magnesium carbonate and the deposition thereof on the support material should be carried out jointly. The precipitation conditions are selected so that the proportion of the precipitate comprising basic magnesium carbonate is present in as sparingly soluble a form as possible. The green catalyst obtained in the precipitation step is, according to the invention, only partially washed so that little precipitated basic magnesium carbonate is washed out of the green catalyst. The invention includes the controlled subsequent alkalization of the partially washed green catalyst, whereby the required enrichment of the catalyst surface with alkali is achieved. The drying of the green catalyst is not critical. It can be carried out within a relatively broad range of drying conditions, for example in a stream of air at from 50° to 100° C.

A critical feature of the present invention is the relative percentages of metallic nickel and nickel oxide in the reduced catalyst. This can be achieved by reducing the green catalyst using hydrogen. This reduction is to be carried out in such a way that the temperature of 350° to 450° C. and the hydrogen flow rate of 0.25 to 0.75 m/second results in only a partial reduction of the nickel-containing component. A degree of reduction from 48% to 86% has proven to be advantageous.

When used in fixed-bed hydrogenation, the green catalyst is shaped prior to drying, for example into an extrudate, dried, reduced, and used in this form or stabilized after reduction by treatment with small amounts of oxygen in nitrogen in a known manner (H. Blume, W. Naundorf and A. Wrubel, Chem. Techn., volume 15 (1963), page 583).

It has been found that sodium depletion at the surface of the hydrogenation catalyst causes an increase in cleavage and secondary reactions which leads to loss of valuable products. Excessive sodium concentrations at the surface of the hydrogenation catalyst results in an increasing decline in the hydrogenation activity. In addition, there is a tendency to form aldolization products. The sodium content in the surface layer is required in the hydrogenation catalyst for controlling the selectivity and thus for suppressing cleavage and secondary reactions. The increased sodium concentration in the surface layer is achieved by slurrying the green catalyst in an alkali solution.

Magnesium depletion at the surface of the hydrogenation catalyst engenders an altered pore structure which is unfavorable compared with the catalyst of the invention. It also provides an increase in the catalyst activity which leads, particularly in the hydrogenation temperature range above 100° C., to the formation of undesired by-products, especially cleavage products; a large magnesium excess causes inactivation and thus lowers the performance of the hydrogenation catalyst.

The examples below serve to illustrate the present invention without limiting it.

PREPARATION EXAMPLE

Preparation of the hydrogenation catalyst 1906 g of $Ni(NO_3)_2 \cdot 6H_2O$ and 355.6 g of $Mg(NO_3)_2 \cdot 6H_2O$ are dissolved in 10.4 liters of water at 99° C. 1500 g of anhydrous $Na_2CO_3$ are dissolved in 14 liter of water at 99° C. in a reactor equipped with a stirrer. While stirring vigorously, the Ni-Mg solution is then introduced at a uniform rate into the sodium carbonate solution over a period of 3 minutes. 230 g of kieselguhr is added in powder form and the suspension formed is stirred for a further 3 minutes and subsequently filtered. The filter cake is washed with 27 liters of water at a temperature of 70° C. The last wash water running off has a conductivity of 1800 µS.

The filter cake is suspended in 6000 g of a 0.25% by weight sodium hydroxide solution, stirred for 2 hours at 50° C., and filtered on a filter press. The filter cake formed is treated with compressed air for 1 minute. The filter cake contains 82% water; in this form, the filter cake is formed into pellets (6 mm diameter). The shaped filter cake is dried in a drying chamber for 5 hours at 50° C., 3 hours at 60° C., and for 8 hours at 75° C. to a constant weight.

The green catalyst had the following analysis:

| | |
|---|---|
| Ni | 37.8% by weight |
| Mgo | 5.2% by weight |
| $Na_2O$ | 1.1% by weight |
| $CO_2$ | 6.0% by weight |
| Support material | 22.7% by weight |
| Moisture | 6.5% by weight |
| Bulk density | 530 g/l |

The green catalyst is reduced at 425° C. over a period of 4 hours. For this purpose, 6 standard $m^3$/hour of reduction gas are passed over 2 kilograms of green pelletized catalyst. The reduction gas comprises 99.5% by volume of hydrogen and 0.5% by volume of nitrogen. A weight loss of 0.76 kilograms is observed on reduction. For a total nickel content of 53% by weight, a degree of reduction of 72% is determined in the reduced catalyst.

APPLICATION EXAMPLE 1

Hydrogenation of n-butanal

The catalyst prepared according to the Preparation Example, in the form of 6 mm pellets (250 ml), is first brought to 120° C. at a heating rate of 20° C./hour in a stream of hydrogen of 730 standard liters/hour at 4 bar in a tube reactor provided with a heating/cooling jacket (internal diameter: 32 mm). After reaching 120° C., 50 ml/hour of n-butanal (liquid) is fed into the vaporizer which is upstream of the reactor and through which 730 standard liters/hour of $H_2$ flow, at a vaporizer temperature of 100° C. The $H_2$/butanal-vapor mixture is heated to the reactor temperature in a preheater which is also upstream of the reactor. After 12 hours, the n-butanal feed rate is increased to 75 ml/hour and, after a further 12 hours, is increased to 100 ml/hour. Thereafter, the butanal feed is increased in steps of 25 ml/hour at intervals of 24 hours. During the increase in the butanal feed, the preheater and reactor temperatures are simultaneously increased as follows:

| n-Butanal feed (ml/h) | Time (h) | Preheater/reactor temperature (°C.) |
| --- | --- | --- |
| 200 | 24 | 123 |
| 225 | 24 | 126 |
| 250 | continuous operation | 128 |

The amount of $H_2$ is kept constant during the feed increase period and during the continuous operation.

The hydrogenation product obtained in vapor form is condensed and analyzed. It comprises 99.9% by weight of n-butanol and contains less than 0.1% by weight of unconverted n-butanal as well as<20 ppm of di-n-butyl ether as an unwanted by-product. In addition to the hydrogenated product, about 0.4 kg of steam per kg of n-butanal used is obtained at>1.8 bar during continuous operation (the steam pressure corresponds to the reactor temperature).

APPLICATION EXAMPLE 2

Hydrogenation of propanal

The catalyst prepared according to the Preparation Example, in the form of 6 mm pellets (250 ml), is first heated to 125° C. at a heating rate of 20° C./hour in a stream of hydrogen (730 standard liter/hour) at 3.5 bar in the reactor system described in Application Example 1. Liquid propanal is then fed into the vaporizer at an initial rate of 50 ml/hour for a period of 12 hours. The propanal feed rate is increased at intervals of 12 hours by 25 ml/hour each time up to 150 ml/hour. On reaching the feed rate of 150 ml/hour, the preheater and reactor temperatures are increased to from 128° to 130° C.

The hydrogenation product obtained is condensed by cooling and analyzed. It comprises about 99.9% by weight of n-propanol and less than 0.1% by weight of unconverted propanal. By-products determined are less than 100 ppm of 2-methylpentan-3-one and less than 20 ppm of di-n-propyl ether. As in Application Example 1, it is also possible to obtain steam ($\geq 1.3$ bar) in the hydrogenation of propanal with the catalyst of the invention.

APPLICATION EXAMPLE 3

Hydrogenation of i-butanal

For the hydrogenation of i-butanal, the catalyst (250 ml) of the Preparation Example is heated to 120° C. under hydrogen under the same conditions as in Application Example 1. Subsequently, 50 ml/hour of i-butanal is introduced. Hydrogenation pressure (3.5 bar), reactor temperature (120° C.), and $H_2$ feed rate (730 standard liters/hour) are kept constant. The resulting hydrogenation product comprises $\geq 99.95\%$ by weight of i-butanol and contains $\leq 0.03\%$ by weight of unconverted i-butanal and less than 20 ppm of di-i-butyl ether. The hydrogenation of i-butanal on the catalyst of the invention generated steam at $\geq 1.8$ bar.

COMPARATIVE EXAMPLE

Hydrogenation of n-butanal

In the same tube reactor described in Application Example 1, 250 ml of the commercial nickel catalyst 55/5 TST (HOECHST AG) in the form of 6 mm pellets is heated to 100° C. at a heating rate of 20° C./hour in a stream of hydrogen of 730 standard liter/hour at 3.5 bar. 50 ml/hour of liquid n-butanal is then fed into the vaporizer upstream of the reactor, the vaporizer being at 100° C. and having 730 standard liters/hour of hydrogen flowing therethrough. Prior to entering the reactor, the hydrogen butanal vapor mixture is heated to the reactor temperature in a preheater. After 12 hours, the feed rate of n-butanal is increased to 75 ml/hour and is increased at intervals of 12 hours up to 150 ml/hour.

These reaction conditions result in a hydrogenation product which contains 98.9% by weight of n-butanol, 0.3% by weight of acetals, 0.3% by weight of trimeric aldolization products of the butanal, 0.1% by weight of hydrocarbons, 0.1% by weight of 2-ethylhexanol, 0.1% by weight of di-n-butyl ether, and from 200 to 300 ppm of butyric acid butyl ester. Of the n-butanal used, from 1.0 to 1.2% by weight are converted via hydrogenolysis into propane and methane which are contained in the outflowing hydrogen stream.

In contrast to the catalyst of the invention, use of the commercial catalyst gives considerable amounts of unwanted by-products, even at 100° C. A particular difficulty in the isolation of pure n-butanol is the distillative removal of the di-n-butyl ether which, with increasing ester contents, leads to disproportionate losses of n-butanol. A further disadvantage, compared to the catalyst of the invention, is the relatively high loss of the desired product (more than 1% by weight) caused by hydrogenolysis.

If the feed of n-butanal is increased to above 150 ml/hour, there is an increase in the formation of di-n-butyl ether and cleavage products as a result of hydrogenolysis. The same effects occur on raising the hydrogenation temperature. In comparison with the catalyst of the invention, the catalyst of the prior art enables a maximum conversion of only 60% of the amount of aldehyde, with the hydrogenation products obtained also being more contaminated. A further disadvantage is the limiting of hydrogenation temperature to a maximum of 100° C., at which no usable steam can be obtained.

While only a limited number of specific embodiments of the present invention have been expressly disclosed, it is, nonetheless, to be broadly construed, and not to be limited except by the character of the claims appended hereto.

What we claim is:

1. A hydrogenation catalyst consisting essentially of in the reduced state

25% to 50% by weight of metallic nickel

10% to 35% by weight of nickel oxide

4% to 12% by weight of magnesium oxide

1% to 5% by weight of sodium oxide the remainder being a water insoluble support material, wherein the total of said nickel and said nickel oxide is 40% to 70% by weight based on said catalyst, said catalyst having a total BET surface area of 80 to 200 $m^2/g$ and a total pore volume, determined by mercury porosimetry, of 0.35 to 0.6 ml/g, said total volume consisting of 30% to 60% of said volume from pores having pore radii equal to or less than 40 Å, 4% to 10% of said volume from pores having pore radii from more than 40 Å to 300 Å, and 30% to 60% of said volume from pores having pore radii from more than 300 Å to 5000 Å.

2. The hydrogenation catalyst of claim 1 wherein 5 to 10 atomic layers closest to the surface thereof contain, as determined by SAM analysis, 18 to 30 atom % of Ni, 1.2 to 3.0 atom % of Na, and 2.8 to 4.8 atom % Mg.

3. The hydrogenation catalyst of claim 2 wherein said atomic layers contain 20 to 28 atom % of Ni, 1.5 to 2.5 atom % of Na, and 3.2 to 4.5 atom % of Mg.

4. The hydrogenation catalyst of claim 1 wherein said metallic nickel has a surface area of 100 to 130 $m^2/g$, as determined by chemisorption of hydrogen.

5. The hydrogenation catalyst of claim 2 wherein said metallic nickel has a surface area of 100 to 130 $m^2/g$, as determined by chemisorption of hydrogen.

6. The hydrogenation catalyst of claim 1 wherein said support material consists essentially of a compound selected from the group consisting of aluminum oxide and silicon dioxide.

7. The hydrogenation catalyst of claim 6 wherein said support material is selected from the group consisting of silicic acid, silica gel, kieselguhr, and siliceous earth.

8. A process for the preparation of the hydrogenation catalyst of claim 1 comprising mixing solutions of a nickel salt, a magnesium salt, sodium carbonate in water to cause precipitation, adding said support material to the mixed solutions and forming a green catalyst in a mother liquor, separating said green catalyst from said mother liquor, partial washing of said green catalyst with water, slurrying said green catalyst in an aqueous alkali solution to form an alkali treated catalyst, separating said alkali-treated catalyst from said slurry, drying said alkali-treated catalyst to form a dried green catalyst, reducing said dried catalyst with hydrogen until 48% to 86% by weight based on a total of said nickel and said nickel oxide is said metallic nickel.

9. The process of claim 8 wherein said precipitation is effected by stirring an aqueous solution, which is at a temperature of 95° to 100° C., containing 0.5 to 0.8 mol/liter of said nickel salt and 0.1 to 0.2 mol/liter of said magnesium salt, into a 0.9 to 1.1 molar aqueous solution of sodium carbonate at a temperature of 95° to 100° C., the molar ratio of $Na_2 CO_3/(Ni+Mg)$ being 1:0.6 to 0.65, to form a catalyst suspension, immediately adding said support material to said catalyst suspension over a period of 0.5 to 5.0 minutes to form said green catalyst, filtering said green catalyst from said mother liquor, partially washing said green catalyst with hot water until said hot water running off said green catalyst has a conductivity of 1500 to 2000 μS, to form a partially-washed catalyst, suspending said partially-washed catalyst in 1 to 3 times its volume of water to form a suspended catalyst, introducing either 0.06 to 0.08 mol of an aqueous solution of sodium hydroxide or 0.03 to 0.04 mol of sodium carbonate per mol of nickel contained in said total of said metallic nickel and said nickel oxide to form a slurry, stirring said slurry at 40° to 60° C. for 1 to 5 hours, and separating said green catalyst from said slurry.

10. The process of claim 8 wherein said dried green catalyst is reduced at a reduction temperature of 350° to 450° C. by contacting said dried green catalyst with 0.5 to 5.0 standard cubic meters per hour of a reduction gas per kilogram of said dried green catalyst, said reduction gas containing 80% to 100% by volume of hydrogen.

11. The process of claim 10 wherein said dried green catalyst is contacted with 1 to 3 standard cubic meters per hour of said reduction gas per kilogram of said dried green catalyst.

\* \* \* \* \*